US 8,204,713 B2

(12) United States Patent
Blick (10) Patent No.: US 8,204,713 B2
(45) Date of Patent: Jun. 19, 2012

(54) NORMALIZED DECIMAL EQUIVALENT SYSTEMS AND METHODS

(76) Inventor: Kenneth E. Blick, Edmond, OK (US)

( * ) Notice: Subject to any disclaimer, the term of this patent is extended or adjusted under 35 U.S.C. 154(b) by 396 days.

(21) Appl. No.: 12/543,427

(22) Filed: Aug. 18, 2009

(65) Prior Publication Data

US 2010/0050116 A1   Feb. 25, 2010

Related U.S. Application Data

(60) Provisional application No. 61/089,857, filed on Aug. 18, 2008.

(51) Int. Cl.
*G06F 17/18* (2006.01)
*G06F 3/048* (2006.01)

(52) U.S. Cl. ........ 702/179; 715/764; 715/808; 715/833; 708/100; 708/304; 708/422; 708/445; 708/490

(58) Field of Classification Search .................. 702/179, 702/100, 304, 422, 445, 490; 715/764, 808, 715/833
See application file for complete search history.

(56) References Cited

U.S. PATENT DOCUMENTS

| | | | |
|---|---|---|---|
| 5,908,788 A * | 6/1999 | Kell | ............................... 436/111 |
| 5,955,370 A | 9/1999 | Kell | |
| 2004/0260178 A1 | 12/2004 | Kahn et al. | |
| 2007/0161921 A1 | 7/2007 | Rausch | |

FOREIGN PATENT DOCUMENTS

EP    1 704 818    9/2006

OTHER PUBLICATIONS

International Search Report for PCT/US2009/054158, mailed on Apr. 7, 2010, 3 pages.
Written Opinion of the International Searching Authority for PCT/US2009/054158, mailed on Apr. 7, 2010, 6 pages.

* cited by examiner

*Primary Examiner* — Sujoy Kundu
(74) *Attorney, Agent, or Firm* — Maier & Maier, PLLC (57) ABSTRACT

A results reporting system can generate test results at one or more laboratory sites. Each of the generated test results can be in a conventional unit of measurement. The results reporting system can then convert each of the testing results to a normalized decimal equivalent unit system of measurement. The normalized decimal equivalent unit of measurement can be a unit of measurement that is normalized to an associated reference range of the test result. Once converted to normalized decimal equivalent unit, the test results can be stored in a mass storage device for later reporting. A triggering event (e.g., a request from a reviewing entity) can then trigger the reporting system to generate a results report using the stored test results. The results report can convey the test results to a reviewing entity using the normalized decimal equivalent unit of measurement in graphs, tables or other methods of conveying data. In some embodiments, result reports can be displayed on a computer display and can include selectable icons that, when selected, display additional information related to the displayed results.

10 Claims, 4 Drawing Sheets

NORMALIZED DECIMAL EQUIVALENT SYSTEMS AND METHODS

CROSS-REFERENCE TO RELATED APPLICATION

This application claims priority to U.S. Provisional Patent Application No. 61/089,857 filed on Aug. 18, 2008, entitled "Normalized Decimal Equivalent Systems and Methods", the contents of which are incorporated by reference herein in their entirety.

FIELD OF THE INVENTION

The disclosed embodiments relate generally to test result reporting systems.

BACKGROUND OF THE INVENTION

The interpretation of clinical laboratory tests commonly involves a concept in comparing a patient's results to a laboratory test "reference range." In general, a reference range can be a set of values used by a health professional to interpret a set of medical test results. In some instances, the range may be defined as a set of values 95% of the normal population falls within. The reference range is also commonly referred to as the "normal range" or "reference interval." For simplicity, the term "reference range" is used herein.

The use of reference ranges can complicate the interpretation of numerical laboratory results, however. For example, some conventional reference range systems present physicians with a plethora of units and numerical results, each of which can vary significantly between laboratories. Even within a particular laboratory, numerical laboratory results and associated reference ranges can vary due to, for example, the methods, specimen types, and instruments employed. Accordingly, there can be variations with the "normal" patients used in the development of reference ranges between sexes, age groups, and races. This can further add to the confusion.

Computer storage of results using reference ranges can also be complicated. For example, some systems may transfer and store reference ranges with the associated laboratory results. Further, some systems may require use of reference range tables stored on hospital systems sharing laboratory data and strictly match those tables to those on a laboratory computer system. With the latter option, archived data on information systems and associated reports can often times be invalid, because reference ranges frequently change with newer diagnostic methods, and archived data may have been generated based on diagnostic methods based on older, out-of-date reference ranges. On some computers systems, a laboratorian may need to develop additional codes for newer diagnostic methods and store new ranges using new results codes. Hence, more permanent results codes may need to be linked to multiple results codes in order to have accurate readings. On the other hand, if reference ranges are stored with each associated result, reports on archived data may be generated much more readily. However, storing a laboratory result with an associated reference range can require additional storage space.

Another challenge has been with regards to data portability. In recent years, patients may be referred to a number of different point-of-care sites (e.g., clinics, emergency rooms, doctor's office, etc.). Each of these point-of-care sites may use different diagnostic methods and instrumentation and, thus, reference ranges and results may likewise vary significantly between point-of-care sites due to the use of different diagnostic methods and instrumentation. Accordingly, a standardization of all laboratory data, regardless of the testing method, could be very useful; especially as patients move between various points-of-care.

A further challenge can relate to displaying data in a useful format. Graphing and trending multiple laboratory results on laboratory computers and computerized spreadsheets can be complicated due to the use of varying units, ranges, and resulting scale variations between various analytes (as referred to herein, an "analyte" can be any substance that is quantified or detected by an experimental procedure). For this reason, plotting three or fewer variables on a chart can be many times the most that can be displayed without making the chart too complicated to read and use. On the other hand, if all laboratory results where normalized, plotting and displaying a large number of test results could be possible on the same graph using a single scale.

Another challenge can relate to providing an intuitive method and system for analyzing and reporting results. A problem with conventional laboratory results reporting is that results are many times not intuitive. For example, physicians often times have to memorize or refer to separate reference range charts to interpret results. To accommodate this deficiency, some laboratory computers can generate "result flags" for high and low results, critical results, and flags that signify results are beyond delta range checks. Notification limits can also be printed and flagged on the chart report. These additional flags, or letters, are many times cryptic and poorly understood by physicians, however. They can also clutter the report and make trending and tracking of results more difficult.

Yet another challenge can be data clutter. Printing reference ranges on reports may be needed in some instances, as these ranges may need to be present for proper interpretation of results. In some instances, section of the report containing the references reference ranges can take up significantly space on the printed report, and, at times, may even take up more space than the actual test results. As a result, it may be difficult and time consuming for physicians to locate pertinent laboratory data in some conventional reports.

Storage of measurement data can provide another challenge. Storage of measurement units with results can take up a substantial amount of memory capacity. If units are included on the reference ranges, additional storage space is typically needed. Moreover, some laboratories and hospitals, due to disk storage limitations, purge laboratory data to tape after thirty days, for example. This can make the purged data unavailable for trending and tracking purposes. However, if laboratory results could be stored without reference ranges and without units, more memory storage capacity could be made available, thereby allowing laboratory results to remain potentially available or "on-line" for a longer period of time.

Consequently, as discussed above, the present methods and systems of reporting numerical laboratory results have many deficiencies. Accordingly, there is a need for new methods and systems for reporting test results that solves some or all of the above-described deficiencies.

SUMMARY OF EMBODIMENTS OF THE INVENTION

In accordance with various embodiments of the present invention, a unique results reporting system can normalize the reporting of numeric laboratory results with one or more of the following attributes: 1) reference ranges can be reflected in one or more result; 2) results that can be compared regardless of the underlying factors (e.g., instrument, age, sex, specimen etc.) affecting a result; 3) out-of-range results that can be intuitive, obviating the need for result flags; 4) concomitant storage of reference ranges and units may no longer be needed; and 5) a new results reporting system can be readily convertible to conventional reporting values and units so the system could be employed without the loss of valuable archived laboratory information.

Conversion of raw laboratory data to a decimal equivalent scale can have a significant number of advantages, including: 1) more intuitive reporting of results, thereby eliminating the need for physicians to memorize reference ranges; 2) comparability of results regardless of method, age, sex, etc.; 3) less computer storage and retrieval requirements as compared to raw data equivalents; 4) elimination or reduction of the need for printing reference ranges and flags for interpretation on physician reports; 5) simplified storage of archival data; 6) better portability between laboratories of test results; 7) more adaptable to graphical reporting of data on computer screens and hand held physician modules; and 8) more concise laboratory reports with less "data" clutter, thereby making pertinent data easier to find.

BRIEF DESCRIPTION OF THE DRAWINGS

For a better understanding of the aforementioned embodiments of the invention as well as additional embodiments thereof, reference should be made to the Detailed Description of the Embodiments below, in conjunction with the following drawings in which like reference numerals refer to corresponding parts throughout the figures.

DETAILED DESCRIPTION OF EXEMPLARY EMBODIMENTS

Methods and systems for normalizing results are described. In the following description, for the purposes of explanation, numerous specific details are set forth in order to provide a thorough understanding of the present invention. It will be apparent, however, to one skilled in the art that the present invention may be practiced without some of these specific details. In other instances, well-known structures and devices are shown in block diagram form.

According to various embodiments of the present invention, a results reporting system can generate test results at one or more laboratory sites. Each of the generated test results can be in conventional unit of measurement. The results reporting system can then convert each of the testing results to a normalized decimal equivalent unit system of measurement, which can be referred to herein as a "CentiBlick" or "CB" unit of measurement. Exemplary implementations of converting test results from a first unit of measurement to a CentiBlick unit of measurement are described in more detail later in this disclosure. Once converted to CentiBlick units, the test results can be stored in a mass storage device for later reporting. A triggering event (e.g., a request from a reviewing entity) can then trigger the reporting system to generate a results report using the stored test results. The results report can convey the test results to a reviewing entity using the CentiBlick unit of measurement in graphs, tables or other methods of conveying data. In some embodiments, result reports can be displayed on a computer display and can include selectable icons that, when selected, display additional information related to the displayed results.

There are many uses for result reporting systems. For example, result reporting systems may be used in a healthcare test reporting environment. In such an environment, a patient's laboratory test results, for example, can be converted into CentiBlick units of measurement. A report can then be generated for conveying the results to a reviewing entity, such as the patient's physician or other health-care professional. The report can display the laboratory results in the CentiBlick units of measurement in a table, graph or other format that is convenient and easy for the reviewing entity to understand and interpret. Of course, the health-care environment is merely one exemplary environment in which embodiments of the present invention can be implemented. For example, various embodiments can be used in other environments in which reference ranges are utilized to interpret numeric results. Specific examples include vital sign measurements in the intensive care unit, growth parameters, and other medical measurements where a reference range is employed.

Figure 1:
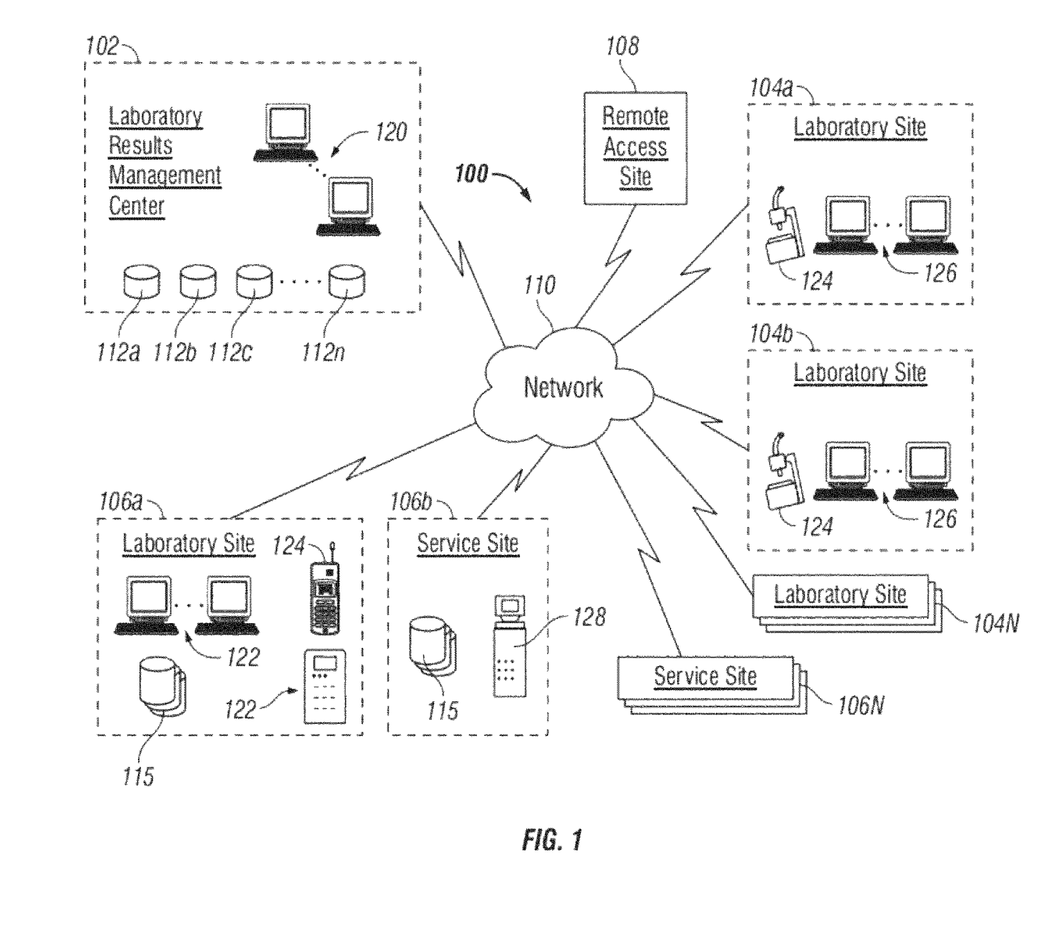
FIG. 1 is a block diagram illustrating an exemplary implementation of a results reporting system in accordance with some embodiments.

Having thus described an example environment for a reporting system of the present invention, it now may be useful to describe an example configuration of the system. FIG. 1 is a diagram illustrating an example implementation of an overall reporting system 100 in accordance with one embodiment of the present invention. Referring now to FIG. 1, the results reporting system 100 can include laboratory results management center 102 in communicative contact with various other elements of the reporting system 100. In one embodiment, laboratory results management center 102 is implemented to provide a centralized management center for providing laboratory results services, features and functions. In alternative embodiments, the services, features and functions provided by laboratory results management center 102 as described herein can be distributed across a plurality of various facilities or locations as would be apparent to one of ordinary skill in the art after reading this description.

The exemplary embodiment of laboratory results management center 102 is illustrated in FIG. 1 as including one or more computers or work stations 120 to facilitate operation thereof. Laboratory results management center 102 can also include one or more databases 112a, 112b, 112c-112n to store the various data and other information used in laboratory results reporting process. As the above examples illustrate, data can be maintained relating to normalized and/or non-normalized laboratory results data, reference ranges associated with laboratory results, client specific information, computer-readable instructions for performing data analysis and reporting, and other information used for processing and managing test result data. Although separate database units are illustrated, data storage can be across any physical or logical data storage architecture, and any of a number of database models can be implemented. In one embodiment, a relational database structure is used to facilitate creation of responses from various separate sources of data.

Referring still to FIG. 1, results reporting system 100 can include one or more appropriate laboratory sites 104A, 104B-104N to provide test result information to laboratory results management center 102. In general, laboratory sites 104 can include laboratory testing equipment 124 used to perform laboratory tests on samples, for example, for generating test result data. The test result data can then be inputted into one or more computers or servers 126 and transmitted to laboratory results management center 102 for further processing, analysis and/or storage. In some embodiments, laboratory site 102 can be largely automated, but in other embodiments, many of the functions performed at laboratory site 102 can be performed manually.

To better illustrate the functionality that can be included with laboratory site 104, consider an example where a doctor obtains a sample from a patient for laboratory testing. The doctor, or person assisting the doctor, may then send the sample to laboratory site 104. The laboratory site 104 can be geographically located close to where the doctor obtained the sample, e.g., in the same hospital or doctor office, or the laboratory site 104 can be located geographically remote from where the doctor obtained the sample. In the later example, the doctor, or person assisting the doctor, may send the sample to the laboratory site 104 via mail or other means of shipping. Once received at the laboratory site 104, the sample may be tested using laboratory testing equipment 124, for example. Results and/or related information about the results from the laboratory testing can then be inputted into computer 126 and some or all of that information can be subsequently transmitted to laboratory results management center 102. In accordance with various embodiments, the test result data can include numerical values of the test results as well as reference ranges associated with the test results.

With further reference to FIG. 1, laboratory results management center 102 is configured to provide various facilities with an appropriate response upon the occurrence of one or more various events. An example of one such event can be a request from a facility for information relating to test results. Examples of a few possible configurations for such requesting facilities are provided in FIG. 1 and referred to as service sites 106A, 106B-106N. Examples of specific types of service sites 106 can include hospitals, doctor offices, nurse satiations, pharmacies and other health-care related sites. As such, in various embodiments of the invention, laboratory results management center 102 or other like mechanism can be provided to perform a variety of laboratory results management functions in support of these various service sites. For example, a hospital, doctor office or other service site 106 may handle various forms of laboratory results analysis and reporting on a daily basis, yet it may not be practical for such a service site 106 to itself maintain the knowledge and other skill sets necessary to properly handle the results reporting it deals with on a daily basis. As such, laboratory results management center 102 in communication with one or more service sites 106 can provide the services, instructions, information, reporting, and other responses that service sites 106 may use, exclusively or as a complement to their own capabilities, to properly handle results reporting in the course of their business.

As stated above, laboratory results management center 102, whether centralized or distributed, can in one embodiment provide result reporting management functionality to a plurality of service sites 106 in geographically diverse locations. The example illustrated in FIG. 1 depicts service sites 106A, 106B-38N illustrating that multiple service sites 106 of different types and configurations can be serviced by the laboratory results management center 102 in one embodiment.

Referring still to the FIG. 1, in the illustrated example, two particular service site 106 configurations are illustrated as service site 106A and service site 106B. Each of these example configurations are now described, although other service site configurations are contemplated within the spirit and scope of the current invention.

To better describe a configuration of service site 106A it is useful to describe it in terms of a specific example. Consider the example where service site 106A is a hospital. Whether the hospital is large or small, most hospitals include some form of computerization to assist in their storage and retrieval of medical records and other hospital related operations.

Service site 106A is illustrated as including one or more computers or servers 122, one or more data repositories 115 and a remote user interface 124. For example, terminals at a nurse station or office may be used to enter information regarding hospital related operations. Each of these systems can be connected to a computer system 122 and data repository 115 to maintain medical records other functions. Computers 122 and data bases 115 may be dedicated devices, configured to perform the laboratory results reporting and analysis functions. In other environments, computers 122 and data bases 115 may be those used for other operations at the hospital that have been provided with the software or other capabilities to perform the laboratory results and reporting functions described herein. Various levels of integration between computers 122, data bases 115 and other facility resources can be provided as may be desired to facilitate operations.

In the illustrated embodiment, one or more remote input devices 124 can also be included to allow remote and portable access to service site computers 106 as well as laboratory results management center 102 (or other aspects of laboratory results system 100 from various locations in or near the service site 106A). Such access may be via numerous mechanisms such as a personal computer or laptop; a PDA, smartphone or other handheld computing device; a telephone; or other appropriate interface mechanism. Remote input devices 124 are not necessarily limited to laboratory results reporting and analysis functions, but can also be used in the conduct of other facility operations.

A wired or wireless communication link between the remote user interface 124 and computer system 122 can be provided to facilitate communication between the devices. Additionally, in one embodiment, a direct communication link between a remote terminal 124 and other elements of the results reporting system 100 (including, for example, laboratory results management center 102) can be provided as well.

In one embodiment, remote user interface 124 can be implemented as a hand-held, battery operated device with a wireless interface allowing the user flexibility and mobility of operation. In addition to wireless communications, a hard wired interface can be included including, for example, a docking station, cradle, or other like device to allow the remote user interface to be charged as well as to transfer data to other components within the system 100.

To better illustrate the functionality that can be included with a remote terminal 124, consider an example where a doctor is making rounds to patients in a hospital. In this example, the doctor can use the remote terminal 124 to access patient medical records and other information to facilitate diagnosis and treatment of patients. In this regard, a doctor can access a patient's test results from the remote terminal 124, thereby providing the doctor with flexibility and mobility of operation. In accordance with embodiments of the present invention, the test results may be provided to the doctor in normalized decimal equivalent units (CentiBlick units). Furthermore, these test results may be displayed on the remote terminal in graph, table or some other format, and the doctor may interact with the remote terminal 124 to obtain further information about the test results.

To illustrate yet another example configuration of a service site 106, reference is now made to service site 106B were in a kiosk 128 is provided to assist with the results reporting functions. Kiosk 128 can be used in addition to or in place of a remote user interface 124 or other input device. Kiosk 128 can provide a walk-up terminal in one embodiment that allows a user to perform results reporting functions such as, for example, requesting and receiving laboratory result information, instructions, and other responses from the laboratory results management center 102.

To better illustrate the functionality that can be included with the kiosk 128, consider an example where a patient supplied a laboratory with specimens to laboratory site 104a for testing. Once the testing is completed, the laboratory site 104 can send the test results to laboratory results management center 102, where the test results are converted into CentiBlick units and stored. The patient can then access and review the test results from the kiosk. In accordance with some embodiments, the kiosk 128 can display the test results in an easily understandable fashion, such as in a graph or table. Furthermore, in some embodiments, the patient may obtain further information about the test results by interacting with the kiosk 128.

Although two exemplary configurations for a service site 106 have been provided, these examples will serve to illustrate to one of ordinary skill in the art after reading this description that other configurations and architectures for service site 106 can be implemented to achieve the features and functions of the results reporting system 100 as described herein. Additionally, the results reporting system 100 can be implemented in such a way as to be scaled to handle a large number of various and diverse service sites 106.

Various elements of result reporting system 100 may also include various communication components to enable communications among themselves as well as with outside entities. For example, communications interfaces to enable communication across network 110 or other communication channels between and among the various results reporting system can be provided. The depicted example illustrates a communications interface implemented via network 110. Although a single network cloud is depicted in FIG. 1, communications among the various elements of results reporting system can take place via any number of different communication channels or mechanisms, and are not necessarily confined to communication across a single local or wide area network. For example, communication elements such as the internet, the public switched telephone network (PSTN), other public an private networks, cellular links, satellite links, and other communication channels can be used alone or in various combinations to provide the elements of communication between and among the various combinations of results reporting system. Thus, it is not necessary that all communication among the elements flow through a single communication network.

Also illustrated in FIG. 1 is a remote access site 108. One or more remote access sites 108 can be provided to allow various users to access the results reporting system 100 from one or more remote locations. Thus, persons with the proper levels of clearance or authorization may be granted remote access privileges to the results reporting system 100. Such remote access may provide the capabilities to, for example, monitor results reporting management activities; gather information about the results reporting process, including various events and responses; conduct operations, and otherwise access the features and functionality of the results reporting system 100 from a location outside of the system.

For example, a user may be provided with access information to log onto the materials management system from his or her home, from on the road, or from some other remote location. Such access may be via numerous mechanisms such as a personal computer or laptop; a PDA, smartphone or other handheld computing device; a telephone; or other appropriate interface mechanism. As such, personnel may maintain contact with the system 100 from various locations.

Figure 2:
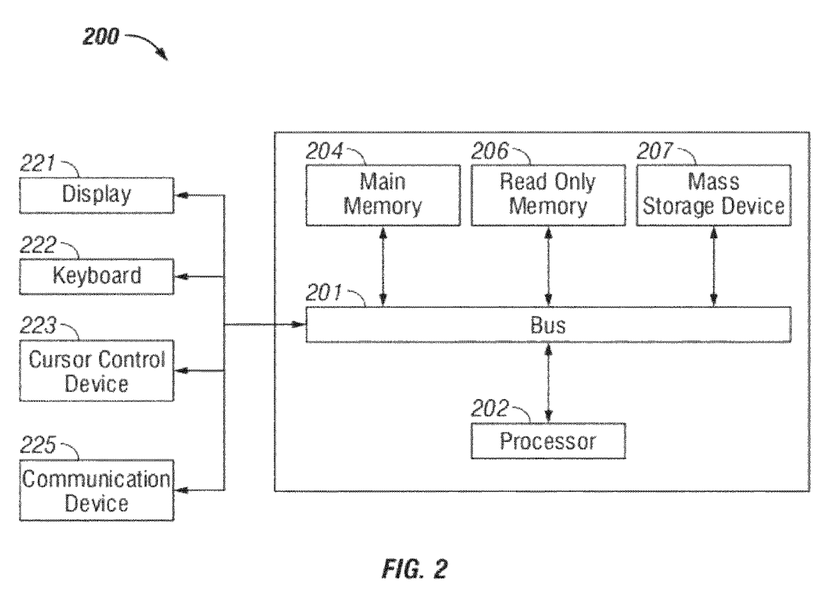
FIG. 2 illustrates an example computer system upon which embodiments of the present invention can be implemented in accordance with some embodiments.

A computer system 200 representing an exemplary service computer in which features of the present invention may be implemented will now be described with reference to FIG. 2. The computing system 200 can represent, for example, a desktop, laptop, and notebook computers; hand held computing devices (PDA's, cell phones, palmtops, etc.); mainframes, supercomputers, or servers; or any other type of special or general purpose computing devices as may be desirable or appropriate for a given application or environment.

The computer system 200 can include a bus or other communication means 201 for communicating information, and a processing means such as processor 202 coupled with bus 201 for processing information. Computer system 200 can further include a random access memory (RAM) or other dynamic storage device 204 (referred to as main memory), coupled to bus 201 for storing information and instructions to be executed by processor 202. Main memory 204 also may be used for storing temporary variables or other intermediate information during execution of instructions by processor 202. Computer system 200 can also have a read only memory (ROM) and/or other static storage device 206 coupled to bus 201 for storing static information and instructions for processor 202.

A data storage device 207 such as a magnetic disk or optical disc and its corresponding drive can also be coupled to computer system 200 for storing information and instructions. Computer system 200 can be coupled via bus 201 to a display device 221, such as a cathode ray tube (CRT) or Liquid Crystal Display (LCD), for displaying information to a computer user. Typically, an alphanumeric input device 222, including alphanumeric and other keys, may be coupled to bus 201 for communicating information and/or command selections to processor 202. Another type of user input device can include cursor control 223, such as a mouse, a trackball, or cursor direction keys for communicating direction information and command selections to processor 202 and for controlling cursor movement on display 221.

In addition, a communication device 225 can be coupled to bus 201 for accessing remote servers via the network 100, for example. The communication device 225 can include a modem, a network interface card, or other commercially available network interface devices, such as those used for coupling to an Ethernet, token ring, or other type of network. In any event, in this manner, the computer system 200 can be coupled to a number of servers and/or other services via a conventional network infrastructure, such as a company's Intranet and/or the Internet, for example.

An exemplary process 300 for converting a test result to a normalized decimal equivalent unit of measurement (CB) will now be described with reference to FIG. 3. The various tasks performed in connection with this processes may be performed by hardware, software, firmware, or any combination thereof. It should be appreciated that this process may include any number of additional or alternative tasks, the tasks shown in FIG. 3 need not be performed in the illustrated order, and this process may be incorporated into a more comprehensive procedure or process having additional functionality not described in detail herein. For illustrative purposes, the following description of processes may refer to elements mentioned above in connection with FIGS. 1-2.

In step 302, results management center 102 can receive test result data generated by laboratory site 104. The test result data can include one or more test results in conventional units and their associated reference ranges.

Next, in step 304, process 300 converts the test results from conventional units to CentiBlick (normalized decimal equivalent units). In this regard, reference ranges for Gaussian data can be divided into four quadrants: mean−2 SD (Standard Deviation), mean−1 SD, mean+1 SD and mean+2 SD. Each quadrant can be assigned 25 decimal equivalents on the CentiBlick unit system, each unit of which can be referred to as a CentiBlick unit (CB). The CentiBlick unit system can have various scales. In one embodiment, the CB scale ranges from 0 to 100, where a value of 0 corresponds to the low end of the reference range, a value of 50 corresponds to the midpoint of the reference range, and a value of 100 corresponds to the high end of the reference range. Values less than 0 can then be considered falling below normal and values greater than 100 can be considered as falling above normal values. Of course, one need not use a 0 to 100 scale, but can use other ranges, such as 0 to 10, 0 to 1000 or the like, depending upon user preference.

To better illustrate, consider the example of an exemplary potassium reference range of 3.5 to 6.5 mmol/L. This reference range has a mean of 5 with a SD=+/−1.5 mmol/L. This reference range can be converted to a 0 to 100 scale, with 50 as the mean. A potassium result of 5 mmol/L would correspond to a value of 50 in the CB scale and indicate that the result is in the middle of what would be considered the normal. A potassium result of 2 mmol/L would correspond to −25 CB, indicating that the result falls below the normal reference range. In contrast, a potassium result of 8 mmol/L would correspond to 125 CB, indicating that the result falls above the normal reference range. Thus, a doctor or other reviewing entity can quickly and easily discern where a test result falls relative to a reference range using the CentiBlick scale. In other words, a reviewing entity need not compare the In accordance with various embodiments, expression (1), below, describes a relationship between CentiBlick (CB) units and conventional units (CU) for within reference range results:

$$CU = SF \times CB + L \qquad (1)$$

In expression (1), Cu is a value in conventional units, CB is a value in CB units, L is a low-end reference range limit; and SF is a scaling factor. The scaling factor can be calculated using expression (2)

$$SF = (H-L)/SR \qquad (2)$$

In expression (2), H is a high-end reference range limit, and SR is a scale range, i.e. a range in which normal values would fall between using the CentiBlick scale. For example, if the CentiBlick scale range is 0 to 100, then SR would have a value of 100.

Expression (1) can then be solved for CB, resulting in expression (3):

$$CB = (CU-L)/SF \qquad (3)$$

Therefore, by computation of a scaling factor and the lower limit of the conventional reference range, conventional unit values can be converted to decimal equivalent (CentiBlick) values.

In accordance with various embodiments, a 100 unit scale has been chosen. The reason for this was 1) to avoid the use of decimals; 2) so that negative results could be readily recognized as below reference range results for analytes; 3) so that multiples of the upper and lower limits could be easily discerned; and 4) to generally expand the reference range scale. In addition, by changing the scale of numerical results, one no longer need be concerned with Gaussian and non-Gaussian range differences. Of course other units of scale can be used instead of the 100 unit of scale in accordance with embodiments of the present invention. For example, a scale from 0 to 1, 0 to 10, 0 to 1000 or other scales can be used.

Using a 100 unit scale, results having values that fall between 0 to 100 can correspond to "in range" results. A 100 unit scale can also approximate percentiles and, hence, laboratory results can be easily understood and explained to patients. Thus, reference to a range using this system can be referred to as "apparent percentiles." For example, a 10 CB result on a patient's cholesterol test can indicate that 90 percent of the age and sex matched population have higher cholesterol values. This can indicate that this cholesterol level falls into a "low normal" portion of the reference range.

For "out-of-range" results (i.e. results that fall outside of the reference range), the Centiblick or CB system can employ multiples of the upper and lower limits of the reference range. Accordingly, a test result having CB value of 200 can mean that it is twice the upper limit of normal. On the other hand, a test result having 120 CB value can indicate that it is 20 percent higher than the upper limit. A test result having a −50 CB value can indicate that it is 50 percent below the low end of the reference range.

Decimal equivalent values for out-of-range results can be determined based on the decimal equivalents of the low (L) and high (H) values as using expressions (4) and (5), respectively:

$$CB(\text{High Results}) = CU \times 100/H \qquad (4)$$

$$CB(\text{Low Results}) = -(100 - CU \times 100/L) \qquad (5)$$

Accordingly, out-of-range high and low values can be expressed as multiples of the high (H) and low (L) values, respectively, using the CentiBlick scale. To convert out-of-range high results back to conventional units (CU), one need only convert the CB value to decimal and multiply it times the upper limit of the reference range. For conversion of out-of-range low CB results back to CU, one need only convert the CB to decimal, multiply times the lower limit, and then subtracts the result from the lower limit.

Figure 3:
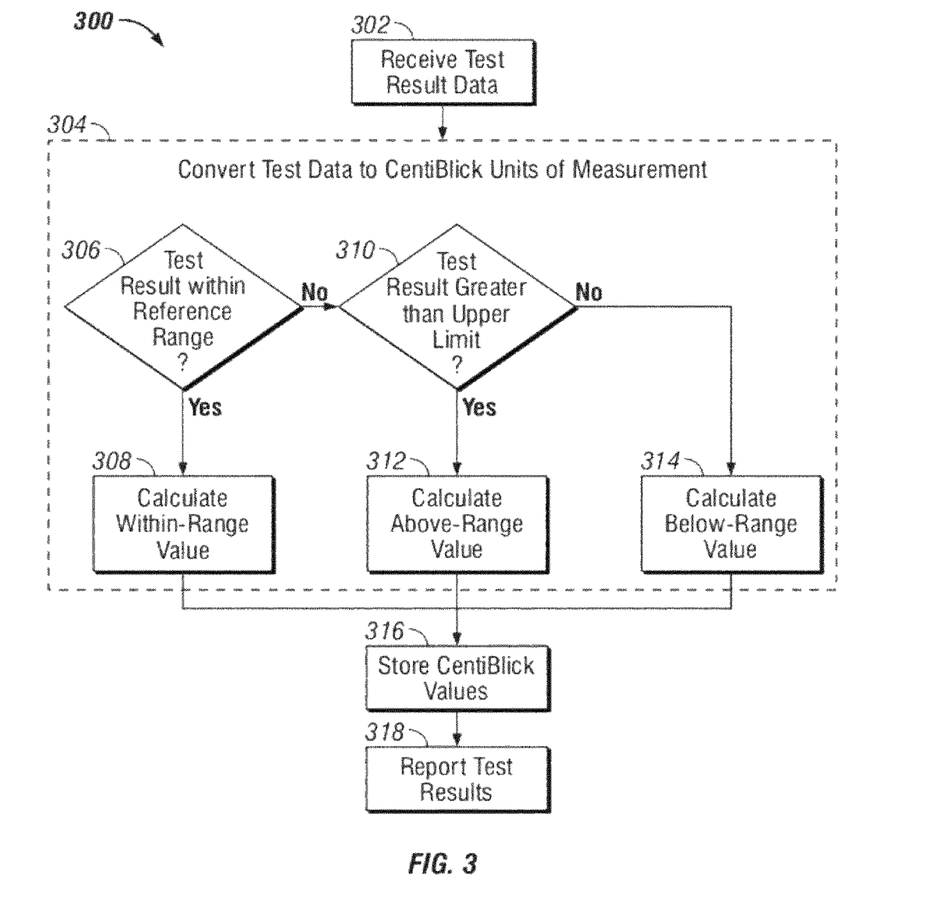
FIG. 3 illustrates an exemplary process for reporting decimal equivalent values in accordance with some embodiments.

Further to FIG. 3, step 304 can include various sub-processes for converting the result data to CentiBlick units, depending upon whether the results fall within the reference range or out of the reference range. Accordingly, in step 306, process 300 determines whether the test results fall within the associated reference range. If so, then process calculates a CentiBlick "within range" value using expression (3) in step 308. If the test result is determined to be an "out of range' result, however, then process 300 proceeds to decisions step 310. In decision step 310, process 300 determines whether the test result is greater than the high-end of the reference range. If so, then process calculates an "above-range" Centiblick value using expression (4). If the test result is not greater that the high-end value in step 310, then process calculates a "below-range" Centiblick value in step 314 using expression (5).

Process 300 can then store the Centiblick values. For example, the Centiblick values can be stored in database 112 in the system of FIG. 1. As discussed above, the associated reference ranges need not be stored because the CentiBlick values take the reference range into account. Should the reference range be needed, one could calculate the high and low end values of the reference range by using expressions (4) and (5) and solving for the high and low end reference range variables, for example.

Finally, process 300 can then report the test results using the CentiBlick values in step 318. As discussed herein, the various methods may be used to report the values, including sending the data to a handheld computer and displayed on the computer for easy and convenient test analysis and interpretation.

Table A below illustrates various exemplary analyte tests and corresponding values of the test results in conventional units (CU) and CentiBlick units (CB). Table A also provides the high and low end cut offs for respective reference ranges of each analyte test in conventional units.

| Analyte Test | H | L | CU Value | CB calc |
|---|---|---|---|---|
| Ca | 10.3 | 7.3 | 8.8 | 50.0 |
| Na | 146 | 136 | 146 | 100.0 |
| Cortisol | 25 | 7 | 23 | 88.9 |
| Folate | 2.5 | 1.5 | 1.6 | 10.0 |
| Theophyline | 20 | 10 | 16 | 60.0 |
| K | 6 | 3.5 | 4 | 20.0 |
| Ca | 10.3 | 7.3 | 14.3 | 138.8 |
| Na | 146 | 136 | 121 | −11.0 |
| Cortisol | 25 | 7 | 49 | 196.0 |
| Folate | 2.5 | 1.5 | 0.5 | −66.7 |
| Theophyline | 20 | 10 | 31 | 155.0 |
| K | 6 | 3.5 | 1 | −71.4 |

As illustrated in Table A, a 4 mmol/L potassium (K) result in conventional units (CU) can be converted to 20 CB in the CB scale, indicating that the test result is within the normal range. Thus, a reviewing entity need only receive the CentiBlick value to determine that the test result falls within the normal range. In contrast, has the reviewing entity only received the test result in the conventional units (mmol/L), the reviewing entity would have had to memorize the reference range or refer to some other source to determine the reference range in order to interpret the results.

Still referring to Table A, a 8 mmol/L potassium can equal 133 CB on the CB scale, indicating a result 33 percent higher than the upper limit of the normal range. A 2 mmol/L potassium level can equal a −43 CB on the CB scale, indicating a result that is 43 percent below the low end of the normal range. Accordingly, a reviewing entity can interpret test results in CentiBlick units much more easily than in conventional units.

In accordance with various embodiments, an appropriate reference range to be used to convert the test result in conventional units to CentiBlick units can be selected depending upon various types of information. For example, in one embodiment, patient information may be used to select an appropriate reference range. As one skilled in the art can appreciate, a normal test that falls within a normal range for a 55 year old female may be different from a normal range for an 18 year old male. Thus, in accordance with various embodiments of the present invention, patient information, such as the age and sex of the patient, for example, can be used to select an appropriate reference range. Of course other types of information can be used.

Embodiments of the present invention can also support a graphical user interface approach to reporting laboratory/medical measurements or test results. Results can be displayed to the user graphically in CB units allowing the physician to review results using the horizontal or vertical slide bars on the computer screens (including hand held PDA/wireless telephonic devices.)

Figure 4:
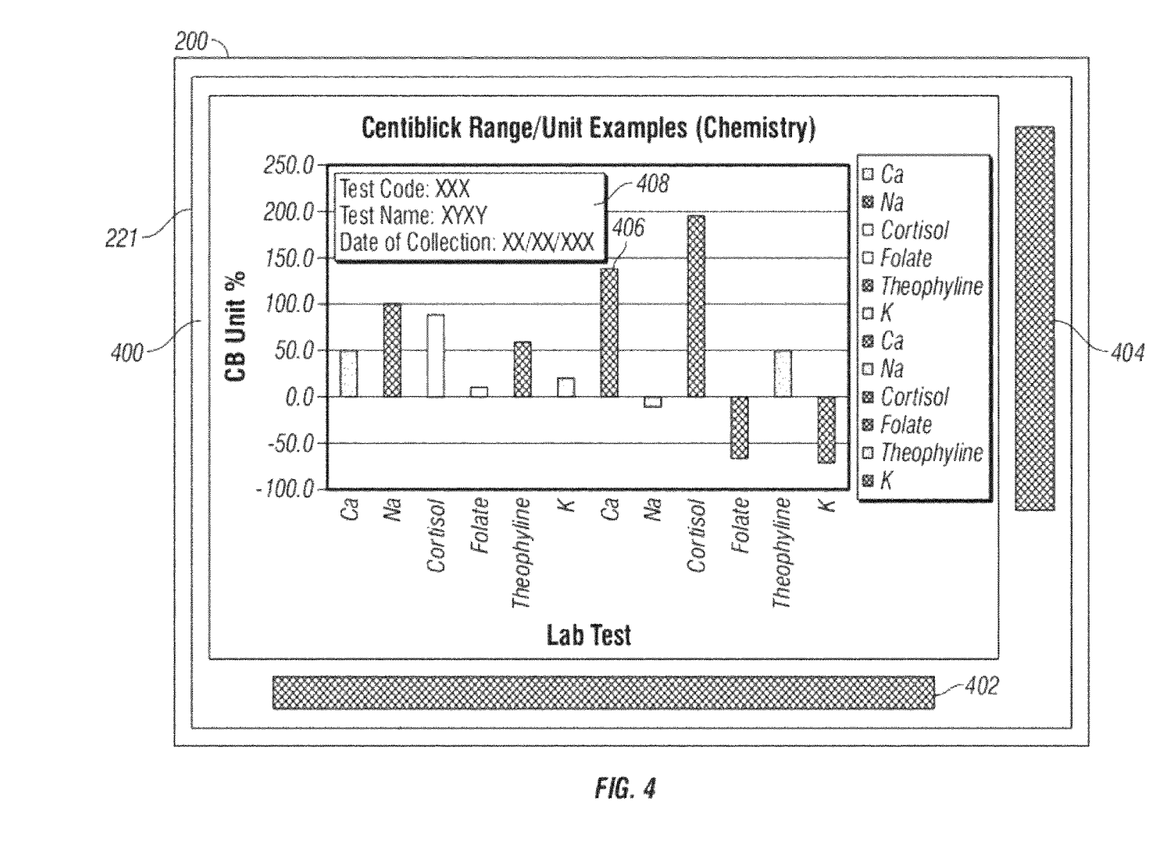
FIG. 4 illustrates an exemplary graphical user interface in accordance with some embodiments.

FIG. 4 illustrates a graphical user interface 400 (hereinafter GUI 400") of a results reporting application on computer 200 in accordance with an exemplary embodiment of the present invention. In this example, the data displayed on GUI 400 is of the test results listed in Table A. As illustrated, the GUI 400 includes a bar graph having a scale from −100 to +250. Laboratory test result names and the associated test results in CB units are displayed on the bar graph. As can be appreciated, a physician can review the entire graph by simply navigating across using a horizontal slide bar 402 then navigating up and down to view abnormal results when encountered using the vertical slide bar 404. Accordingly, a physician can review laboratory and other medical data from 1) different laboratories (reference labs and in hospital labs), 2) different methods within the hospital (point-of-care glucose versus central laboratory) and all other data in one scan.

As an option, a pop up menu or display window can appear on GUI 400 in response to a triggering event, such as a user selecting a selectable area of the GUI 400. In one example, a user can select bar 406 which can cause pop-up box 408 to be displayed on GUI 400. Pop-up box 408 can include information relating to the test result associated with bar 406. This information can include any type of information that may be useful for a reviewing entity to have in analyzing or interpreting the test results. Such information can include an associated test code, test name, date of collection of the test sample, the exact CentiBlick value, a high or low range designation, appended comments from another reviewing entity or laboratory technician, whether the specimen is hemolyzed, the conventional unit value of the test result, the conventional reference range values, measuring units, and the like.

To illustrate, a reviewing entity can trigger a display of traditional results along with the reference ranges (age and sex matched), measurement units, any high and low result flags, and any comments that were appended to the result such as "hemolyzed", "results called", "critical values" by selecting one of the bars in the GUI 400. In addition, important comments that can influence the interpretation of results should be displayed (without requiring a point and click) along with the CB results bar with the color of the text drawing attention to the comment. For example, the comment "hemolyzed" cam be reported in the CB bar display for results like potassium and lactate dehydrogenase (LDH), where hemolysis can have a significant effect on the laboratory result. The reviewing entity can also select a comment in order to document that he/she noted the comment as part of the review process. This verification of comment review feature can be stored for later review logging/documentation/reimbursement purposes.

GUI 400 can also include drop down menus (not shown) for performing other functions on the GUI. Such functions can include changing the scale of graph, options to review other test results, and the like.

Another feature of the new system can allow the same results to be plotted in bar graphs or line graphs on the same scale. For example, liver enzymes can be plotted along with the laboratory therapeutic drug level for a hepatotoxic drug.

Further to FIG. 4, to highlight normal and abnormal results, those results falling within the normal range (0 and 100) can be displayed in a first color, such as green; whereas abnormal results, which fall outside of the normal range, can displayed in a second color, such as red. Furthermore, the shade of the color of the abnormal result can vary depending upon how far the result falls outside of the normal range. For example, a result that is close to the normal range can be in a light shade of red; whereas a result that is far outside the normal range can be a dark shade of red. Also, in accordance with some embodiments, critical results (i.e. those falling far outside the normal range) can flash until the reviewing physician clicks on the bar to verify their review.

In accordance with some embodiments, test results need only be stored on the computer's repository disk medium in one place and not stored as both CB and conventional results. Doing so can promote harmonization between the CB system and the conventional system. Software can then be used to interconvert results as desired when data is needed for review/display, printed reports, research, or other purposes. Indeed, some physicians may elect to look at all medical results using conventional units while other may default to the exclusive use of the CB unit system. Some reviewing entities may elect to use both CB and conventional units and toggle back and forth as needed. The equations for the interconversion between CB and conventional results reporting and storage can be used for this purpose.

In accordance with some embodiments, test results are stored in CB units. This approach can be beneficial in medical clinics were multiple reference laboratories and multiple instruments are used to report the same result. Storing results in CB units can allow these results on the same analyte to be displayed and reviewed simultaneously even though in conventional units, the results can different normal reference ranges and units. Also, within the hospital, point of care testing results for glucose and other analytes can be displayed along with central core laboratory results even though the tests were performed on different analyzers. The CB display bar in this case can contain cursor addressable note icons that indicate the results were obtained using different methods. Placing the cursor on this note icon can display the method used, reference lab name, or core lab indicator for routine in hospital testing.

Hence, the GUI 400 can bring together all laboratory/medical results regardless of the method or origin of the results. Core laboratory, reference laboratory, point-of-care are all to be displayed together for review along with cursor and click addressable icons to allow the reviewing physician to drill down into traditional units, comments, methods, result flags, etc. GUI 400 can allow historic data performed by different methods and instrument, to be simultaneously displayed with the current result after CB conversion. An indicator on the CB display bar can indicate that the results is historic (or "previously reviewed") and can allow the user to select and sort such data based on date range so the data can be trended in real time. Thumbnail line graphs can be used along with the CB bars, where the user can compare two or more medical results on the same graph. Point on the line graphs that have comments can include icons so the user can click and note comments. Comment icons may be added or hidden based on the user's preference.

Note that computer readable instructions implementing processes described herein, can be stored and transported on any computer-readable medium for use by or in connection with an instruction execution system, apparatus, or device, such as a computer-based system, processor-containing system, or other system that can fetch the instructions from the instruction execution system, apparatus, or device and execute the instructions. In the context of this document, a "computer-readable medium" can be any medium that can contain, store, communicate, propagate, or transport the program for use by or in connection with the instruction execution system, apparatus, or device. The computer readable medium can be, for example but not limited to, an electronic, magnetic, optical, electromagnetic, infrared, or semiconductor system, apparatus, device, or propagation medium. More specific examples (a non-exhaustive list) of the computer-readable medium would include the following: an electrical connection (electronic) having one or more wires, a portable computer diskette (magnetic), a random access memory (RAM) (magnetic), a read-only memory (ROM) (magnetic), an erasable programmable read-only memory (EPROM) (magnetic), an optical fiber (optical), portable optical disc such a CD, CD-R, CD-RW, DVD, DVD-R, or DVD-RW, or flash memory such as compact flash cards, secured digital cards, USB memory devices, memory stick, etc. Note that the computer-readable medium could even be paper or another suitable medium upon which the program is printed, as the program text can be electronically captured via optical scanning of the paper or other medium, then compiled, interpreted or otherwise processed in a suitable manner if necessary, and then stored in a computer memory.

The foregoing description, for purpose of explanation, has been described with reference to specific embodiments. However, the illustrative discussions above are not intended to be exhaustive or to limit the invention to the precise forms disclosed. Many modifications and variations are possible in view of the above teachings. The embodiments were chosen and described in order to facilitate explanation of the principles of the invention and its practical applications, to thereby enable others skilled in the art to best utilize the invention and various embodiments with various modifications as are suited to the particular use contemplated.

What is claimed is:

1. A computer-implemented method for normalized decimal equivalents comprising:
   a processor configured to perform the steps of:
   determining whether a test result value having a first unit of measurement is within a reference range associated with the test result; and
   converting the test result value into a second unit of measurement if the test result is within the reference range, using the equation: $CB=(CU-L)/SF$,
   where CB is the value in the second unit of measurement, CU is the value in the first unit of measurement, L is a low-end limit of the reference range and SF is a scaling factor calculated using the equation: $SF=(H-L)/SR$,
   where H is a high-end limit of the reference range, and SR is a scale range with a value of 100.

2. A method of claim 1, further comprising:
   determining whether the test result value is greater than an upper limit of the reference range; and
   converting the test result value into the second unit of measurement if the test result is greater than the upper limit of the reference range, using the equation: $CB=CU\times100/H$,
   where H is equal to the value of the high end limit of the reference range.

3. A method of claim 1, further comprising:
   determining whether the test result value is less than a lower limit of the reference range; and
   converting the test result value into the second unit of measurement if the test result is less than the lower limit of the reference range, using the equation: $CB=-(100-CU\times100/L)$, where L is equal to the value of the low end limit of the reference range.

4. A method of claim 1, further comprising:
   generating test results in the first unit of measurement;
   transmitting the test results in the first unit of measurement to a centralized management center, the centralized management center performing the step of converting the test results from the first unit of measurement to the second unit of measurement; and storing the test results in the second unit of measurement in a memory storage unit.

5. A method of claim 4, further comprising:
transmitting the test results in the second unit of measurement to a mobile computing device; and
displaying the test results in the second unit of measurement of the mobile computing device.

6. An electronic device, comprising:
a display;
one or more processors;
memory; and
one or more programs, wherein the one or more programs are stored in the memory and configured to be executed by the one of more processors, the program including:
instructions for converting a test result in conventional units to decimal equivalent units including:
instructions for determining whether a test result value is within a reference range associated with the test result; and
instructions for converting the test result in the decimal equivalent units using the equation $CB=(CU-L)/SF$ if the test result is determined to be within the reference range, where CB is the value in the second unit of measurement, CU is the value in the first unit of measurement, L is a low-end limit of the reference range and SF is a scaling factor; and
instructions for displaying the test result on the display.

7. An electronic device of claim 6, further comprising instructions for displaying a graphical user interface operable to display the test result in the decimal equivalent units and provide information relating to the test result in response to one or more user inputs.

8. An electronic device of claim 6, further comprising storing the test result decimal equivalent units in the memory.

9. An electronic device of claim 6, wherein the instructions for converting the test result further comprise:
instructions for determining whether the test result value is greater than an upper limit of the reference range; and
instructions for converting the test result value into decimal equivalent units if the test result is greater than the upper limit of the reference range, using the equation $CB=CU\times 100/H$, where H is equal to the value of the high end limit of the reference range.

10. An electronic device of claim 6, wherein the instructions for converting the test result further comprise:
instructions for determining whether the test result value is less than a lower limit of the reference range; and
instructions for converting the test result value into the second unit of measurement if the test result is less than the lower limit of the reference range, using the equation $CB=-(100-CU\times 100/L)$, where L is equal to the value of the low end limit of the reference range.

* * * * *